United States Patent
Hoshino et al.

(10) Patent No.: US 7,692,044 B2
(45) Date of Patent: Apr. 6, 2010

(54) PROCESS FOR PRODUCING CYCLOALKANOL AND/OR CYCLOALKANONE

(75) Inventors: Masahiro Hoshino, Niihama (JP); Nobufumi Watanabe, Niihama (JP)

(73) Assignee: Sumitomo Chemical Company, Limited, Chuo-ku, Tokyo (JP)

( * ) Notice: Subject to any disclaimer, the term of this patent is extended or adjusted under 35 U.S.C. 154(b) by 0 days.

(21) Appl. No.: 12/184,461

(22) Filed: Aug. 1, 2008

(65) Prior Publication Data

US 2009/0036714 A1 Feb. 5, 2009

(30) Foreign Application Priority Data

Aug. 3, 2007 (JP) ............................. 2007-202672

(51) Int. Cl.
*C07C 45/32* (2006.01)
*C07C 35/18* (2006.01)

(52) U.S. Cl. ...................................... 568/357; 568/822

(58) Field of Classification Search .................. 568/357, 568/822

See application file for complete search history.

(56) References Cited

U.S. PATENT DOCUMENTS 6,806,390 B1  10/2004  Herron et al.
2007/0225526 A1  9/2007  Hoshino

FOREIGN PATENT DOCUMENTS

WO  99/40055 A1  8/1999
WO  00/03963 A1  1/2000

OTHER PUBLICATIONS

Carvalho et al. Iron and Copper immobilised on mesorporous MCM-41 molecular sieves as catalysts for the oxidation of cyclohexane. Journal of Molecular Catalysis A: Chemical 144, 1999, p. 91-99.*
S. Samanta, et al., "Mesoporous Cr-MCM-41: An efficient catalyst for selective oxidation of cycloalkanes," Journal of Molecular Catalysis A: Chemical, vol. 36, Jul. 18, 2005, pp. 7-11.
Parasuraman Selvam and Tressia A.P. Paulose, "Transition-Metal (Ti, V, Cr, Mn, Fe, Co, Cu) Containing Ordered Nanoporous Materials: Novel Heterogeneous Catalysts for Selective Oxidation Reactions," Journal of Nanoscience and Nanotechnology, vol. 6, No. 6, Jun. 2006, pp. 1758-1764.
Gaomeng Lu, et al., "Gold nanoparticles in mesoporous mateirals showing catalytic selective oxidation cyclohexane using oxygen", Applied Catalysis A: General 280 (2005) 175-180.
Shaoyong Liu et al., "Liquid-Phase Oxidation of Cyclohexane Using Co-P-MCM-41 Catalyst", Korean J. Chem. Eng., vol. 15, No. 5 (1998) 510-515.

* cited by examiner

*Primary Examiner*—Sikarl A Witherspoon
(74) *Attorney, Agent, or Firm*—Sughrue Mion, PLLC (57) ABSTRACT

An object of the present invention is to provide a process capable of producing cycloalkanol and/or cycloalkanone with a favorable selectivity by oxidizing cycloalkane with a favorable conversion.

Disclosed is a process for producing cycloalkanol and/or cycloalkanone, which comprises oxidizing cycloalkane with oxygen in the presence of mesoporous silica, wherein (1) the mesoporous silica contains at least one transition metal, and (2) a ratio of total volume of mesoporous silica particles having a particle diameter of 20 μm or less to total volume of entire mesoporous silica particles is 25% or more in the mesoporous silica.

7 Claims, 4 Drawing Sheets

PROCESS FOR PRODUCING CYCLOALKANOL AND/OR CYCLOALKANONE

BACKGROUND OF THE INVENTION

1. Field of the Invention

This application was filed claiming Paris Convention priority of Japanese Patent Application No. 2007-202672, the entire content of which is herein incorporated by reference.

The present invention relates to a process for producing cycloalkanol and/or cycloalkanone by oxidizing cycloalkane with oxygen.

2. Description of the Related Art

There are known, as the process for producing cycloalkanol and/or cycloalkanone by oxidizing cycloalkane with oxygen, process for performing the oxidation reaction in the presence of mesoporous silica containing transition metal is known (refer to, for example, Applied Catalysis A: General, Netherlands, 2007, Vol. 318, p. 128-136; Microporous and Mesoporous Materials, Netherlands, 2007, Vol. 99, pp. 334-344; Journal of Nanoscience and Nanotechnology), U.S.A., 2006, Vol. 6, pp. 1758-1764; Journal of Molecular Catalysis A: Chemical, Netherlands, 2006, Vol. 246, pp. 162-166; and Catalysis Letters, Netherlands, 2006, Vol. 108, pp. 49-54).

SUMMARY OF THE INVENTION

The above-mentioned conventional methods sometimes include unsatisfactory points in view of the conversion of cycloalkane and the selectivity of cycloalkanol and/or cycloalkanone. Thus, an object of the present invention is to provide a process capable of producing cycloalkanol and/or cycloalkanone with a favorable selectivity by oxidizing cycloalkane with a favorable conversion.

The present inventors have intensively studied and found that comparatively a lot of mesoporous silica particles having a large particle diameter, for example, mesoporous particles having a particle diameter of more than 20 μm exist in conventional mesoporous silica. As a result of a further intensive study, they have found that the above object can be achieved by performing the above oxidation reaction in the presence of mesoporous silica containing at least one transition metal in which a ratio of total volume of mesoporous silica particles having a particle diameter of 20 μm or less to total volume of entire mesoporous silica particles is a predetermined value or more. Thus, the present invention has been completed.

That is, the present invention provides a process for producing cycloalkanol and/or cycloalkanone, which comprises oxidizing cycloalkane with oxygen in the presence of mesoporous silica, wherein (1) the mesoporous silica contains at least one transition metal, and (2) a ratio of total volume of mesoporous silica particles having a particle diameter of 20 μm or less to total volume of entire mesoporous silica particles is 25% or more in the mesoporous silica.

According to the present invention, cycloalkanol and/or cycloalkanone can be produced with a favorable selectivity by oxidizing cycloalkane with a favorable conversion.

DETAILED DESCRIPTION OF THE INVENTION

The present invention will now be described in detail. In the present invention, the corresponding cycloalkanol and/or cycloalkanone is/are produced by oxidizing cycloalkane used as a starting material with oxygen (molecular oxygen) in the presence of a predetermined mesoporous silica.

Examples of the cycloalkane as the raw material include monocyclic cycloalkanes having no substituent on the ring, such as cyclopropane, cyclobutane, cyclopentane, cyclohexane, cycloheptane, cyclooctane, cyclodecane, and cyclooctadecane; polycyclic cycloalkanes such as decalin and adamantane, and cycloalkanes having a substituent on the ring, such as methylcyclopentane and methylcyclohexane, and also two or more kinds of them can be used, if necessary.

An oxygen-containing gas is usually used as the oxygen source. This oxygen-containing gas may be, for example, air, pure oxygen, or an air or pure oxygen diluted with an inert gas such as nitrogen, argon or helium. Oxygen enriched air obtained by adding pure oxygen to air can also be used.

In the present invention, the above oxidation reaction is performed in the presence of mesoporous silica containing at least one transition metal in which a ratio of total volume of mesoporous silica particles having a particle diameter of 20 μm or less to total volume of entire mesoporous silica particles is a predetermined value or more. Using such mesoporous silica, cycloalkanol and/or cycloalkanone can be produced with a favorable selectivity by oxidizing cycloalkane with a favorable conversion.

Examples of the transition metal to be contained in the mesoporous silica include transition metals having catalytic activity to the above oxidation reaction. Among these transition metals, vanadium, chromium, manganese, iron, cobalt, ruthenium and palladium are preferable, and cobalt is more preferable. If necessary, two or more kinds of these transition metals may be used. The content of the transition metal is usually from 0.01 to 20%, preferably from 0.05 to 10%, and still more preferably from 0.1 to 5%, in terms of a weight ratio of the metal to the mesoporous silica.

The mesoporous silica in the present invention has a so-called mesoporous structure containing pores which usually have a nearly uniform size of 2 to 50 nm, and the surface area thereof is usually from about 600 to 1,500 $m^2/g$. The metal may be incorporated into a silica framework constituting the mesoporous structure, or may be incorporated into the pores, or may be supported on the surface of the silica framework.

Examples of the mesoporous silica include a MCM-41 type mesoporous silica, a MCM-48 type mesoporous silica, a FSM-16 type mesoporous silica, a SBA-15 type mesoporous silica and a HMS type mesoporous silica, among which a MCM-41 type mesoporous silica is preferable. The presence or absence of the mesoporous structure can be confirmed by the presence or absence of a peak $2\theta=0.2$ to $4.0°$ in the measurement of XRD (X-ray diffraction).

The present invention has a feature that a ratio of total volume of small mesoporous silica particles having a particle diameter of 20 μm or less to total volume of entire mesoporous silica particles is 25% or more. As described above, when using mesoporous silica in which a ratio of total volume of mesoporous silica particles having a particle diameter of 20 μm or less to total volume of entire mesoporous silica particles is a predetermined amount or more in the above oxidation reaction, cycloalkanol and/or cycloalkanone can be produced with a favorable selectivity by oxidizing cycloalkane with a favorable conversion. Such a ratio is preferably 35% or more, and more preferably 45% or more.

The above ratio can be determined by measuring particle diameter distribution of the mesoporous silica using a commercially available laser diffraction/scattering particle diameter distribution analyzer, followed by expression on a volume basis. Specifically, the mesoporous silica is dispersed in water (dispersion medium) and the dispersed mesoporous silica particles is irradiated with laser beam, and then the obtained light intensity distribution pattern is detected to obtain light intensity distribution data. Based on the resultant data, particle diameter distribution, that is, distribution of particles having different sizes in different contents is calculated by Fraunhofer diffraction theory or Mie scattering theory, followed by expression on a volume basis. Then, a ratio of total volume of mesoporous silica particles having a particle diameter of 20 μm or less to total volume of entire mesoporous silica particles can be determined from the particle diameter distribution expressed on a volume basis.

The process for preparing mesoporous silica in the present invention will now be described. Examples of the process for preparing silica having a mesoporous structure include (1) a process in which tetraalkoxysilane, a structure-directing agent, ammonia, alcohol and water are mixed and the obtained solid is calcined, and (2) a process in which tetraalkoxysilane, a structure-directing agent, NaF and water are mixed and the obtained solid is calcined. Among these methods, the above-mentioned process (1) is preferable.

Examples of tetraalkoxysilane in the above-mentioned process (1) include tetramethoxysilane, tetraethoxysilane, tetrapropoxysilane, and tetrabutoxysilane, and also two or more kinds of them can be used, if necessary. Among these silanes, tetraethoxysilane is preferable.

Examples of the structure-directing agent in the above-mentioned process (1) include alkyltrimethylammonium bromides having 19 to 21 carbon atoms, such as hexadecyltrimethylammonium bromide, heptadecyltrimethylammonium bromide, and octadecyltrimethylammonium bromide; alkyltrimethylammonium chlorides having 19 to 21 carbon atoms, such as hexadecyltrimethylammonium chloride, heptadecyltrimethylammonium chloride, and octa-decyltrimethylammonium chloride; and alkyltrimethylammonium hydroxides having 19 to 21 carbon atoms, such as hexadecyltrimethylammonium hydroxide, heptadecyltrimethylammonium hydroxide, and octadecyltrimethylammonium hydroxide, and also two or more kinds of them can be used, if necessary. Among these structure-directing agents, alkyltrimethylammonium bromide is preferable, and hexadecyltrimethylammonium bromide is more preferable.

In the above-mentioned process (1), tetraalkoxysilane, a structure-directing agent, ammonia, alcohol and water are mixed. As described above, by mixing ammonia and alcohol, in addition to tetraalkoxysilane, a structure-directing agent and water, and performing a hydrolysis reaction of tetraalkoxysilane and a synthesis reaction of silica, mesoporous silica containing a predetermined amount or more of small mesoporous particles having a particle diameter of 20 μm or less can be prepared.

As ammonia in the process (1), liquid ammonia, gaseous ammonia, or ammonia water may be used. Ammonia water is preferably used. The alcohol in the above-mentioned process (1) can be usually an aliphatic alcohol having about 1 to 6 carbon atoms and specific examples thereof include methanol, ethanol, propanol, butanol, pentanol, and hexanaol. Also two or more kinds of them can be used, if necessary. Among these alcohols, ethanol is preferable.

The amount of the structure-directing agent used in the above-mentioned process (1) is usually from 0.1 to 1.0 mol, and preferably from 0.2 to 0.5 mol, based on 1 mol of the tetraalkoxysilane. The amount of ammonia used in the above-mentioned process (1) is usually from 1 to 50 mol, and preferably from 2 to 25 mol, based on 1 mol of the tetraalkoxysilane. The amount of water used in the above-mentioned process (1) is usually from 5 to 30 parts by weight, and preferably from 10 to 15 parts by weight, based on 1 part by weight of the tetraalkoxysilane. The amount of alcohol used in the above-mentioned process (1) is usually from 5 to 30 parts by weight, and preferably from 10 to 15 parts by weight, based on 1 part by weight of the tetraalkoxysilane.

Examples of the tetraalkoxysilane in the above-mentioned process (2) include tetramethoxysilane, tetraethoxysilane, tetrapropoxysilane, and tetrabutoxysilane, similar to the above-mentioned process (1), and also two or more kinds of them can be used, if necessary. Among these silanes, tetraethoxysilane is preferable.

Examples of the structure-directing agent in the above-mentioned process (1) include alkyltrimethylammonium bromides having 19 to 21 carbon atoms, such as hexadecyltrimethylammonium bromide, heptadecyltrimethylammonium bromide, and octadecyltrimethylammonium bromide; alkyltrimethylammonium chlorides having 19 to 21 carbon atoms, such as hexadecyltrimethylammonium chloride, heptadecyltrimethylammonium chloride, and octadecyltrimethylammonium chloride; and alkyltrimethylammonium hydroxides having 19 to 21 carbon atoms, such as hexadecyltrimethylammonium hydroxide, heptadecyltrimethylammonium hydroxide, and octadecyltrimethylammonium hydroxide, similar to the above-mentioned process (1), and also two or more kinds of them can be used, if necessary. Among these structure-directing agents, alkyltrimethylammonium bromide is preferable, and hexadecyltrimethylammonium bromide is more preferable.

In the above-mentioned process (2), tetraalkoxysilane, a structure-directing agent, NaF and water are mixed. As described above, by mixing with NaF, in addition to tetraalkoxysilane, a structure-directing agent and water, and performing a hydrolysis reaction of tetraalkoxysilane and a synthesis reaction of silica, the desired mesoporous silica as described above can be prepared.

The amount of the structure-directing agent in the above-mentioned process (2) is usually from 0.1 to 1.0 mol, and preferably from 0.2 to 0.5 mol, based on 1 mol of the tetraalkoxysilane. The amount of NaF used in the above-mentioned process (2) is usually from 0.5 to 8 mol, and preferably from 1 to 4 mol, based on 1 mol of the tetraalkoxysilane. The amount of water used in the above-mentioned process (2) is usually from 5 to 30 parts by weight, and preferably from 10 to 15 parts by weight, based on 1 part by weight of the tetraalkoxysilane.

The mixing temperature in the above-mentioned processes (1) and (2) is usually from 20 to 200° C., and preferably from 25 to 150° C. The mixing time is usually from 0.1 to 400 hours, and preferably from 1 to 200 hours.

A solid is produced by mixing as described above. The resultant solid is isolated by filtration, dried and then calcined. Drying is usually performed under an air atmosphere. The drying temperature is from about 40 to 120° C., and the drying time is from about 2 to 24 hours.

Calcination is usually performed under an air atmosphere. The calcination temperature is usually from 450 to 650° C., and preferably from 500 to 600° C., and the calcination time is usually from 4 to 12 hours, and preferably from 6 to 10 hours.

The mesoporous silica in the present invention is silica containing the above-mentioned mesoporous structure, and further contains at least one transition metal. Examples of the process of incorporating the metal into the silica having a mesoporous structure include a process of adding a metal compound such as a halogenate, a nitrate, a sulfate, a carboxylate, an oxo-acid salt or a hydroxide of the metal in the case of mixing in the process for preparation of the silica having a mesoporous structure; a process of impregnating the silica having a mesoporous structure with a solution of the above metal compound; a process of immersing the silica having a mesoporous structure in a solution of the metal compound thereby adsorbing the metal compound to the silica; and a process of ion-exchanging a metal cation of the metal compound with a cation of the silica. The amount of the metal compound used is appropriately adjusted so as to control to obtain the above-mentioned content of the metal.

It is possible to use, as the raw material of the transition metal, vanadium compounds such as vanadium bromide, vanadium chloride, vanadium fluoride, and vanadium naphthate; chromium compounds such as chromium chloride, chromium nitrate, chromium sulfate, chromium acetate, and chromium naphthate; manganese compounds such as manganese bromide, manganese chloride, manganese fluoride, manganese nitrate, manganese ammonium sulfate, manganese sulfate, manganese acetate, and manganese naphthate; iron compounds such as iron bromide, iron chloride, iron fluoride, iron nitrate, iron sulfate, iron acetate, and iron naphthate; cobalt compounds such as cobalt bromide, cobalt chloride, cobalt fluoride, cobalt nitrate, cobalt sulfate, cobalt acetate, cobalt naphthate, and cobalt hydroxide; ruthenium compounds such as ruthenium bromide and ruthenium chloride; and palladium compounds such as palladium bromide, palladium chloride, palladium nitrate, palladium sulfate, and palladium hydroxide. Among these compounds, cobalt compounds are preferable.

Effectively, the mesoporous silica in the present invention is the one which is subjected to a contact treatment with an organosilicon compound. The organosilicon compound can be preferably reacted with the mesoporous silica to bond on the surface, and can be typically represented by the following formula (I):

$$Si(R^1)_x(R^2)_{4-x} \qquad (I)$$

wherein $R^1$ represents an alkoxy group, hydroxy group or a halogen atom, $R^2$ represents an alkoxy group, an alkyl group, an allyl group, an aryl group or an aralkyl group, and x represents a number of 1 to 3.

Examples of the alkoxy group represented by $R^1$ and $R^2$ include a methoxy group, an ethoxy group, a propoxy group and a butoxy group, and examples of the alkyl group represented by $R^2$ include a methyl group, an ethyl group, a propyl group and a butyl group. Examples of the aryl group represented by $R^2$ include a phenyl group, a naphthyl group and a tolyl group, and examples of the aralkyl group represented by $R^2$ include a benzyl group and a phenethyl group.

As the organosilicon compound represented by the formula (I), trialkoxyalkylsilane and tetraalkoxysilane are more preferably used.

The process of subjecting to a contact treatment with an organosilicon compound includes, for example, a process of immersing the mesoporous silica which does or does not contain the metal in a liquid containing an organosilicon compound; and a process of bringing a gas containing an organosilicon compound into contact with the mesoporous silica which does or does not contain the metal.

When the silica having a mesoporous structure without such metal is subjected to the contact treatment, it is possible to incorporate the metal similar to above by impregnating the silica subjected to the contact treatment with a solution of the metal compound, or immersing the silica subjected to the contact treatment in a solution of the metal compound.

The amount of the organosilicon compound used is usually from 1 to 10,000 parts by weight, preferably from 5 to 2,000 parts by weight, and more preferably from 10 to 1,500 parts by weight, based on 100 parts by weight of the silica before being subjected to the contact treatment.

The temperature of the contact treatment is usually from 0 to 300° C., and preferably from 30 to 250° C. The time for the contact treatment is usually from 0.1 to 50 hours, and preferably from 1 to 20 hours.

Thus, the desired mesoporous silica can be obtained. Then, cycloalkane is oxidized with oxygen in the presence of the mesoporous silica. The amount of the mesoporous silica used in the oxidation reaction is usually from 0.0001 to 50 parts by weight, and preferably from 0.001 to 10 parts by weight, based on 100 parts by weight of the cycloalkane.

The temperature of the oxidation reaction is usually from 0 to 200° C., and preferably from 50 to 170° C., and the reaction pressure is usually from 0.01 to 10 MPa, and preferably from 0.1 to 2 MPa. A reaction solvent can be optionally used and, for example, nitrile solvents such as acetonitrile or benzonitrile, and carboxylic acid solvents such as acetic acid or propionic acid can be used.

A post-treatment after the oxidation reaction is not specifically limited and examples thereof include a process of filtering the reaction mixture thereby separating the catalyst, followed by washing with water and further distillation. When cycloalkyl hydroperoxide corresponding to the cycloalkane as the starting material is contained in the reaction mixture, it can be converted into the objective cycloalkanol and cycloalkanone by alkali treatment or reduction treatment.

EXAMPLES

Hereinafter, the present invention is described by reference to the Examples, but the present invention is not limited thereto. Cyclohexane, cyclohexanone, cyclohexanol and cyclohexyl hydroperoxide in the reaction solution were analyzed by gas chromatography, and the conversion of cyclohexane as well as each selectivity of cyclohexanone, cyclohexanol and cyclohexyl hydroperoxide was calculated from the analysis results.

Reference Example 1

Figure 1:
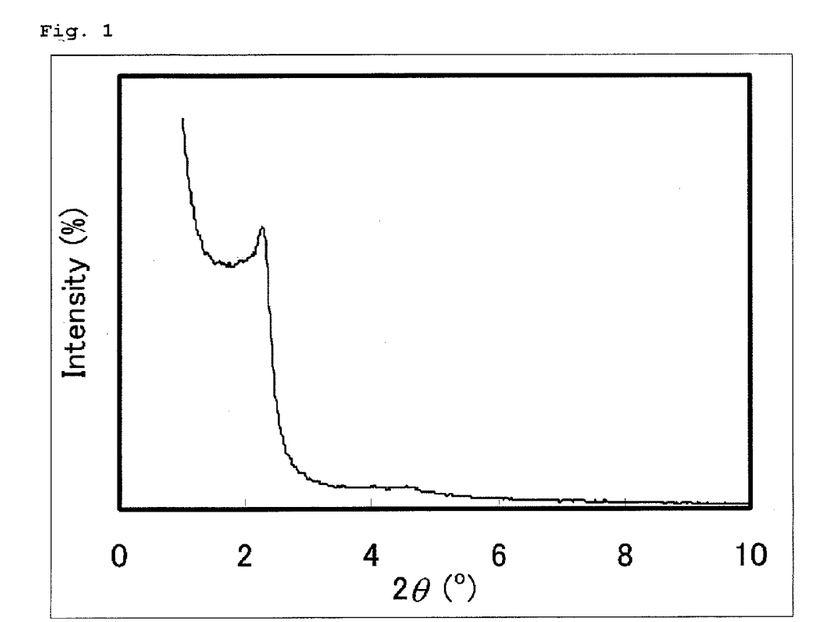
FIG. 1 is a graph showing an XRD pattern of the cobalt-containing mesoporous silica obtained in Reference Example 1(A).

(A) Preparation of Cobalt-Containing Mesoporous Silica 9.56 g of hexadecyltrimethylammonium bromide (manufactured by Wako Pure Chemical Industries, Ltd.), 175.82 g of water, 231.18 g of ethanol (manufactured by Wako Pure Chemical Industries, Ltd.), 0.40 g of cobalt (II) acetate tetrahydrate (manufactured by Wako Pure Chemical Industries, Ltd.), 64.84 g of 25% by weight of ammonia water (manufactured by Wako Pure Chemical Industries, Ltd.) and 18.21 g of tetraethoxysilane (ethyl orthosilicate, manufactured by Wako Pure Chemical Industries, Ltd.) were charged in a 1 L beaker, stirred at room temperature for 16 hours and then hydrothermally synthesized at 90° C. for 7 days. The resulting mixture was filtered, and the residue was washed with water and then dried at 100° C. for 12 hours. The resulting dried product was calcined under an air flow at 550° C. for 7 hours. With respect to the powder obtained by calcination, XRD measurement was conducted using a copper Kα ray. As a result, it was confirmed that a peak peculiar to a mesoporous structure is observed at about $2\theta=2.3°$ and a cobalt-containing mesoporous silica is produced. The XRD pattern is shown in FIG. 1.

(B) Measurement of Particle Diameter Distribution

With respect to the cobalt-containing mesoporous silica obtained in Reference Example 1(A), particle diameter distribution was measured as follows.

A laser diffraction/scattering particle diameter distribution analyzer ["Laser Scattering Size Distribution Analyzer LA-920" manufactured by HORIBA, Ltd.] was used as a measuring device, 623.8 nm He—Ne laser 1 mW and tungsten lamp 50 W were used as a light source of laser beam, and ring-shaped silicon photodiode divided into 75 sections and silicon photodiode were used as a detector.

Figure 2:
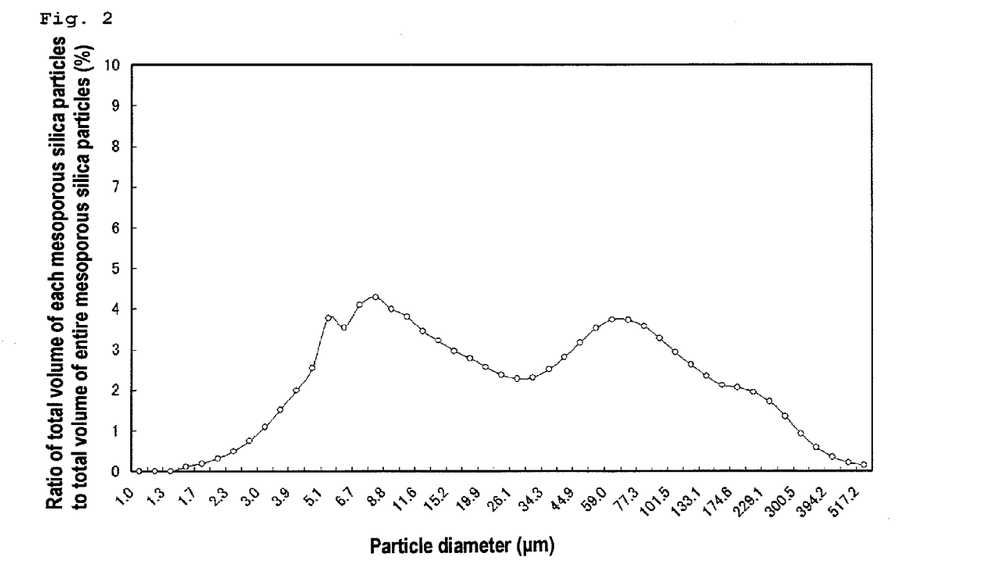
FIG. 2 is a graph showing particle diameter distribution (expressed on a volume basis) of the cobalt-containing mesoporous silica obtained in Reference Example 1(A).

First, about 250 ml of water as a dispersion medium was charged in a sample cell made of Tempax glass. After blank measurement, 30 mg of the cobalt-containing mesoporous silica obtained in Reference Example 1(A) was charged in the sample cell, dispersed for 5 minutes and irradiated with laser beam, and then the measurement was performed at permeability within a range from 65 to 80%. Assuming that a value of a relative refractive index is 1.50, the resultant light intensity distribution data were analyzed to obtain particle diameter distribution expressed on a volume basis. A ratio of total volume of mesoporous silica particles having a particle diameter of 20 μm or less to total volume of entire mesoporous silica particles was calculated. As a result, it was 47%. The particle diameter distribution is shown in FIG. 2.

(C) Measurement of Infrared Absorption Spectrum

Figure 3:
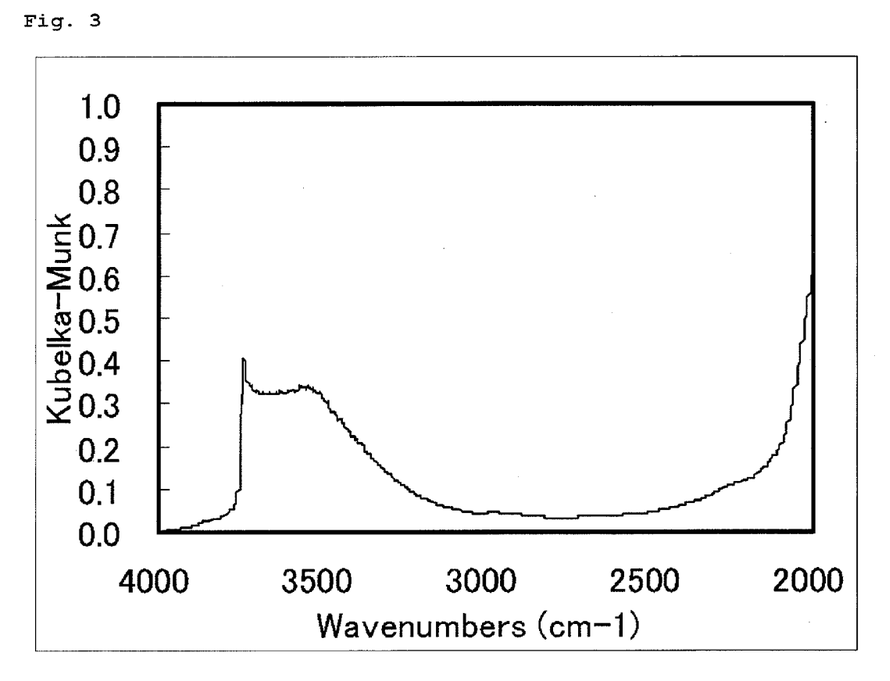
FIG. 3 is a graph showing an infrared absorption spectrum of the cobalt-containing mesoporous silica obtained in Reference Example 1(A).

The cobalt-containing mesoporous silica obtained in Reference Example 1 was charged in a catalytic cell (Diffuse Reflectance Heat Chamber, Model HC900, manufactured by SPECTRA-TECH Co.) and set in an apparatus for measuring an infrared absorption spectrum (Magna 760-ESP, manufactured by NICOLET Co.) and, after deaeration under 0.1 Torr (13 Pa) at 200° C. for one hour, an infrared absorption spectrum was measured. The measuring conditions are as follows: the measuring temperature of 200° C., the measuring pressure of 0.1 Torr (13 Pa), the measuring range of from 400 to 4,000 cm$^{-1}$, and the resolution of 4 cm$^{-1}$. Using data obtained by measuring an infrared absorption spectrum of potassium bromide in the same manner as a background, the resulting data were subjected to Kubelka-Munk conversion. The measurement results of an infrared absorption spectrum of the cobalt-containing mesoporous silica are shown in FIG. 3.

Reference Example 2

(A) Contact Treatment of Cobalt-Containing Mesoporous Silica with Trimethoxypropylsilane 1.0 g of the cobalt-containing mesoporous silica obtained in Reference Example 1(A) and 10.0 g of triethoxypropylsilane (manufactured by Tokyo Kasei Kogyo Co., Ltd.) were charged in a flask and then stirred under a nitrogen atmosphere at 90° C. for 7.5 hours. The resulting mixture was cooled to room temperature and ethanol was added, followed by stirring and further filtration. The residue was washed with ethanol, dried under 0.1 Torr (13 Pa) at 40° C. for one hour and then dried at 100° C. Thus, a cobalt-containing mesoporous silica subjected to a contact treatment with trimethoxypropylsilane was obtained.

(B) Measurement of Infrared Absorption Spectrum

An infrared absorption spectrum of the cobalt-containing mesoporous silica subjected to a contact treatment with trimethoxypropylsilane obtained in Reference Example 2(A) was measured in the same manner as in Reference Example 1(C). The results are shown in FIG. 4.

Figure 4:
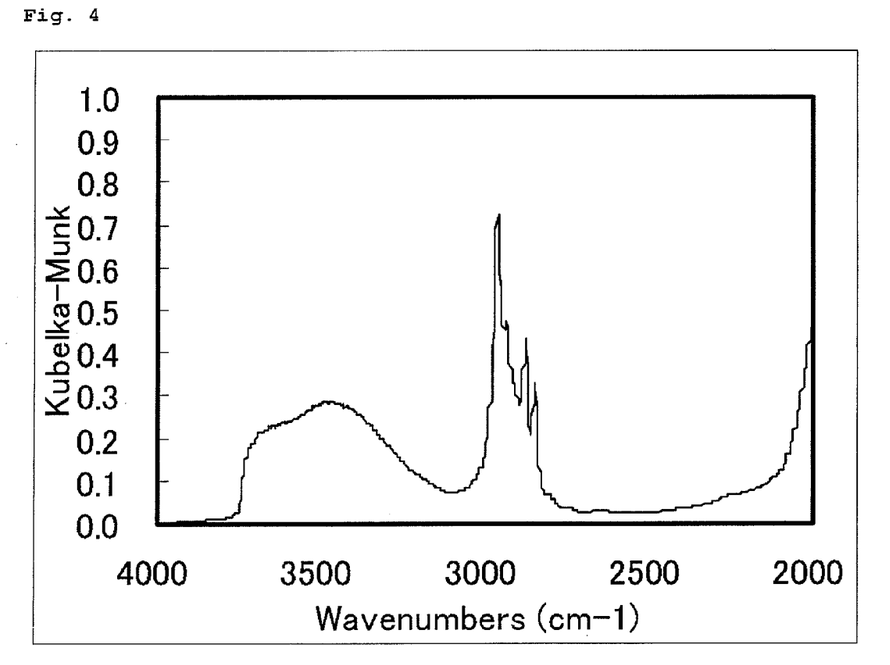
FIG. 4 is a graph showing an infrared absorption spectrum of the cobalt-containing mesoporous silica subjected to a contact treatment with trimethoxypropylsilane obtained in Reference Example 2(A).

As shown in FIG. 3, a peak attributed to a so-called terminal silanol group is observed at about 3,740 cm$^{-1}$ in the cobalt-containing mesoporous silica obtained in Reference Example 1(A), while, as shown in FIG. 4, the same peak is not observed in the cobalt-containing mesoporous silica subjected to a contact treatment with trimethoxypropylsilane obtained in Reference Example 2(A) and it is considered that the terminal silanol group is silylated with trimethoxypropylsilane.

Reference Example 3

Figure 5:
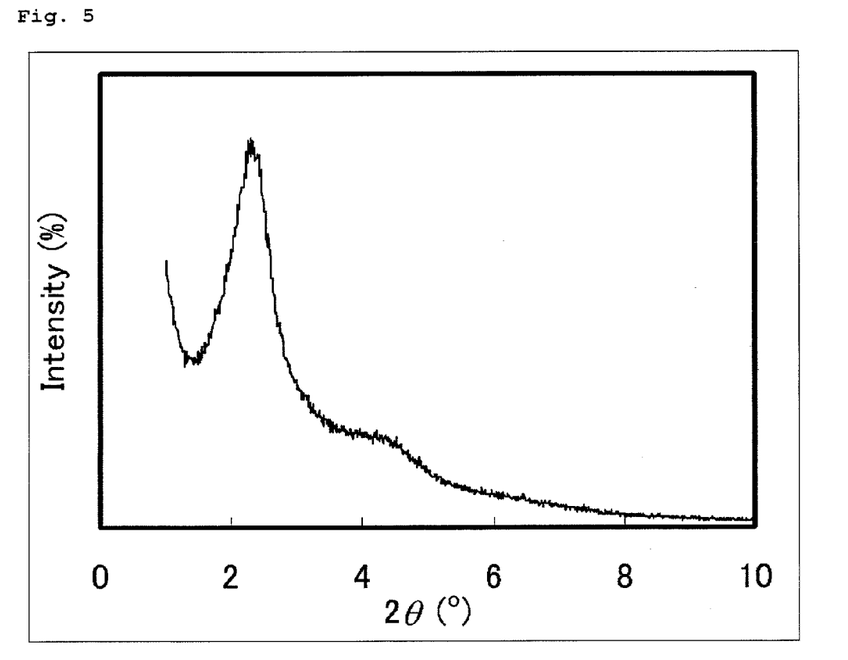
FIG. 5 is a graph showing an XRD pattern of the cobalt-containing mesoporous silica obtained in Reference Example 3(A).

(A) Preparation of Cobalt-Containing Mesoporous Silica 5.44 g of hexadecyltrimethylammonium bromide (manufactured by Wako Pure Chemical Industries, Ltd.), 56.25 g of water, 14.59 g of an aqueous 7.5 wt % solution of sodium hydroxide (manufactured by Wako Pure Chemical Industries, Ltd.), 20.72 g of tetraethoxysilane (ethyl orthosilicate, manufactured by Wako Pure Chemical Industries, Ltd.) and 3.00 g of an aqueous 15 wt % solution of cobalt (II) acetate tetrahydrate (manufactured by Wako Pure Chemical Industries, Ltd.) were charged in a 200 ml beaker, stirred at room temperature for 16 hours and then hydrothermally synthesized at 90° C. for 7 days. The resulting mixture was filtered, and the residue was washed with water and then dried at 100° C. for 12 hours. The resulting dried product was calcined under an air flow at 550° C. for 7 hours. With respect to the powder obtained by calcination, XRD measurement was conducted using a copper Kα ray. As a result, it was confirmed that a peak peculiar to a mesoporous structure is observed at about $2\theta=2.3°$ and a cobalt-containing mesoporous silica is produced. The XRD pattern is shown in FIG. 5.

(B) Measurement of Particle Diameter Distribution

Figure 6:
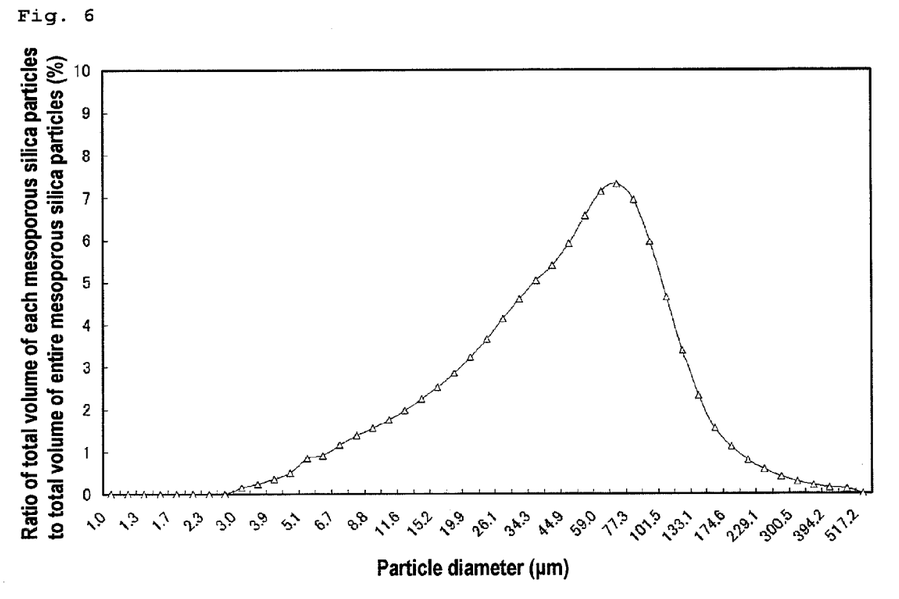
FIG. 6 is a graph showing particle diameter distribution (expressed on a volume basis) of the cobalt-containing mesoporous silica obtained in Reference Example 3(A).

With respect to the cobalt-containing mesoporous silica obtained in Reference Example 3(A), particle diameter distribution expressed on a volume basis was obtained in the same manner as in Reference Example 1(B). A ratio of total volume of mesoporous silica particles having a particle diameter of 20 μm or less to total volume of entire mesoporous silica particles was calculated. As a result, it was 22%. The particle diameter distribution is shown in FIG. 6.

(C) Measurement of Infrared Absorption Spectrum

An infrared absorption spectrum of the cobalt-containing mesoporous silica obtained in Reference Example 3(A) was measured in the same manner as in Reference Example 1(C). The results are show in FIG. 7.

Reference Example 4

(A) Contact Treatment of Cobalt-Containing Mesoporous Silica with Trimethoxypropylsilane 1.0 g of the cobalt-containing mesoporous silica obtained in Reference Example 3(A) and 10.0 g of trimethoxypropylsilane (manufactured by Tokyo Kasei Kogyo Co., Ltd.) were charged in a flask and then stirred under a nitrogen atmosphere at 90° C. for 7.5 hours. The resulting mixture was cooled to room temperature and ethanol was added, followed by stirring and further filtration. The residue was washed with ethanol, dried under 0.1 Torr (13 Pa) at 40° C. for one hour and then dried at 100° C. Thus, a cobalt-containing mesoporous silica subjected to a contact treatment with trimethoxypropylsilane was obtained.

(B) Measurement of Infrared Absorption Spectrum

An infrared absorption spectrum of the cobalt-containing mesoporous silica obtained in Reference Example 4(A) was measured in the same manner as in Reference Example 1(C). The results are show in FIG. 8.

Figure 7:
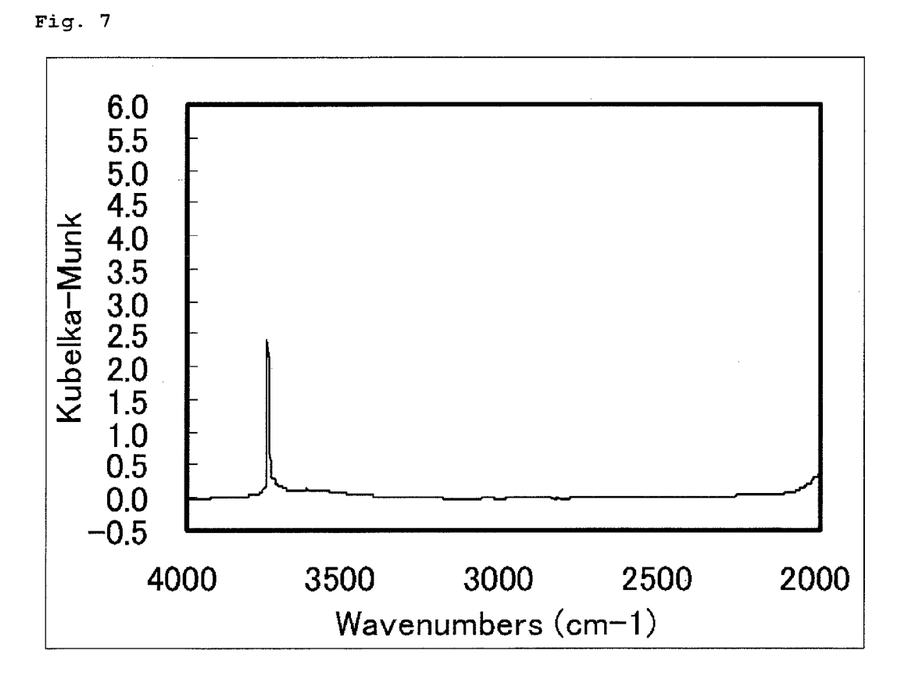
FIG. 7 is a graph showing an infrared absorption spectrum of the cobalt-containing mesoporous silica obtained in Reference Example 3(A).
Figure 8:
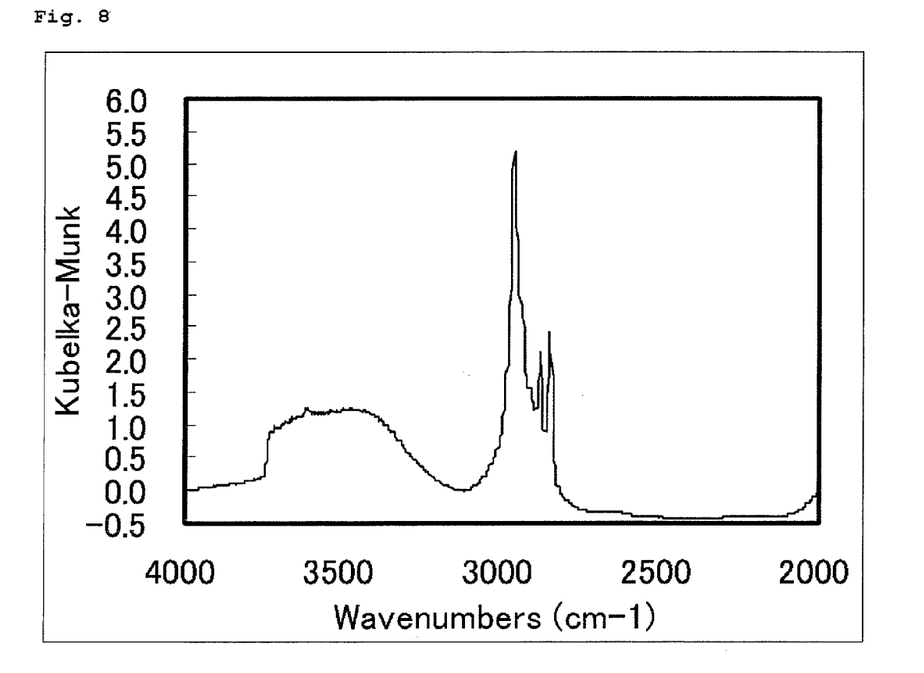
FIG. 8 is a graph showing an infrared absorption spectrum of the cobalt-containing mesoporous silica subjected to a contact treatment with trimethoxypropylsilane obtained in Reference Example 4(A).

As shown in FIG. 7, a peak attributed to a so-called terminal silanol group is observed at about 3,740 cm$^{-1}$ in the cobalt-containing mesoporous silica obtained in Reference Example 3(A), while, as shown in FIG. 8, the same peak is not observed in the cobalt-containing mesoporous silica subjected to a contact treatment with trimethoxypropylsilane obtained in Reference Example 4(A) and it is considered that the terminal silanol group is silylated with trimethoxypropylsilane.

Example 1

In a 1 L autoclave, 278 g (3.3 mol) of cyclohexane and 0.28 g of the cobalt-containing mesoporous silica obtained in Reference Example 1(A) were charged. After increasing the pressure in the system to 0.93 MPa at room temperature using nitrogen and heating to 140° C., the reaction was carried out under the flow of a gas having an oxygen concentration of 15 vol % for 2.5 hours.

1.5 hours after the beginning of the reaction, the conversion of cyclohexane was 6.4%, the selectivity of cyclohexanone was 31.6%, the selectivity of cyclohexanol was 47.5%, and the selectivity of cyclohexyl hydroperoxide was 3.0% (total selectivity: 82.1%). 2 hours after the beginning of the reaction, the conversion of cyclohexane was 8.5%, the selectivity of cyclohexanone was 35.0%, the selectivity of cyclohexanol was 43.6%, and the selectivity of cyclohexyl hydroperoxide was 1.8% (total selectivity: 80.4%). 2.5 hours after the beginning of the reaction (upon completion), the conversion of cyclohexane was 10.9%, the selectivity of cyclohexanone was 37.9%, the selectivity of cyclohexanol was 40.1%, and the selectivity of cyclohexyl hydroperoxide was 1.5% (total selectivity: 79.5%).

Example 2

The same operation as in Example 1 was conducted, except that the cobalt-containing mesoporous silica subjected to a contact treatment with trimethoxypropylsilane obtained in Reference Example 2(A) was used in place of the cobalt-containing mesoporous silica obtained in Reference Example 1(A).

1.5 hours after the beginning of the reaction, the conversion of cyclohexane was 6.7%, the selectivity of cyclohexanone was 32.1%, the selectivity of cyclohexanol was 44.3%, and the selectivity of cyclohexyl hydroperoxide was 6.5% (total selectivity: 82.9%). 2 hours after the beginning of the reaction, the conversion of cyclohexane was 8.8%, the selectivity of cyclohexanone was 35.8%, the selectivity of cyclohexanol was 40.8%, and the selectivity of cyclohexyl hydroperoxide was 5.3% (total selectivity: 81.9%). 2.5 hours after the beginning of the reaction (upon completion), the conversion of cyclohexane was 11.0%, the selectivity of cyclohexanone was 38.4%, the selectivity of cyclohexanol was 38.6%, and the selectivity of cyclohexyl hydroperoxide was 3.0% (total selectivity: 80.0%).

Comparative Example 1

The same operation as in Example 1 was conducted, except that the cobalt-containing mesoporous silica obtained in Reference Example 3(A) was used in place of the cobalt-containing mesoporous silica obtained in Reference Example 1(A).

1.5 hours after the beginning of the reaction, the conversion of cyclohexane was 5.7%, the selectivity of cyclohexanone was 32.2%, the selectivity of cyclohexanol was 44.9%, and the selectivity of cyclohexyl hydroperoxide was 4.7% (total selectivity: 81.8%). 2 hours after the beginning of the reaction, the conversion of cyclohexane was 7.9%, the selectivity of cyclohexanone was 35.1%, the selectivity of cyclohexanol was 42.3%, and the selectivity of cyclohexyl hydroperoxide was 2.3% (total selectivity: 79.7%). 2.5 hours after the beginning of the reaction (upon completion), the conversion of cyclohexane was 10.1%, the selectivity of cyclohexanone was 37.5%, the selectivity of cyclohexanol was 38.2%, and the selectivity of cyclohexyl hydroperoxide was 2.1% (total selectivity: 77.8%).

Comparative Example 2

The same operation as in Example 1 was conducted, except that the cobalt-containing mesoporous silica obtained in Reference Example 4(A) subjected to a contact treatment with trimethoxypropylsilane was used in place of the cobalt-containing mesoporous silica obtained in Reference Example 1(A).

1.5 hours after the beginning of the reaction, the conversion of cyclohexane was 6.1%, the selectivity of cyclohexanone was 32.2%, the selectivity of cyclohexanol was 46.1%, and the selectivity of cyclohexyl hydroperoxide was 2.9% (total selectivity: 81.2%). 2 hours after the beginning of the reaction, the conversion of cyclohexane was 8.2%, the selectivity of cyclohexanone was 35.6%, the selectivity of cyclohexanol was 42.7%, and the selectivity of cyclohexyl hydroperoxide was 1.7% (total selectivity: 80.0%). 2.5 hours after the beginning of the reaction (upon completion), the conversion of cyclohexane was 10.4%, the selectivity of cyclohexanone was 38.0%, the selectivity of cyclohexanol was 38.7%, and the selectivity of cyclohexyl hydroperoxide was 1.7% (total selectivity: 78.4%).

The major embodiments and the preferred embodiments of the present invention are listed below.

[1] A process for producing cycloalkanol and/or cycloalkanone, which comprises oxidizing cycloalkane with oxygen in the presence of mesoporous silica, wherein
(1) the mesoporous silica contains at least one transition metal, and
(2) a ratio of total volume of mesoporous silica particles having a particle diameter of 20 μm or less to total volume of entire mesoporous silica particles is 25% or more in the mesoporous silica.

[2] The process according to [1], wherein the transition metal is at least one metal selected from the group consisting of vanadium, chromium, manganese, iron, cobalt, ruthenium and palladium.

[3] The process according to [1], wherein the transition metal is cobalt.

[4] The process according to any one of [1] to [3], wherein the mesoporous silica is a MCM-41 type mesoporous silica.

[5] The process according to any one of [1] to [4], wherein the mesoporous silica is mesoporous silica obtained by mixing tetraalkoxysilane, a structure-directing agent, ammonia, alcohol and water and calcining the obtained solid.

[6] The process according to any one of [1] to [5], wherein the mesoporous silica is the one which is subjected to a contact treatment with an organosilicon compound.

[7] The process according [6], wherein the organosilicon compound is represented by the following formula (I):

Si(R$^1$)$_x$(R$^2$)$_{4-x}$ (I)

wherein R$^1$ represents an alkoxy group, hydroxy group or a halogen atom, R$^2$ represents an alkoxy group, an alkyl group, an allyl group, an aryl group or an aralkyl group, and x represents a number of 1 to 3.

[8] The process according [6], wherein the organosilicon compound is trialkoxyalkylsilane or tetraalkoxysilane.

[9] The process according to any one of [1] to [8], wherein the cycloalkane is cyclohexane.

What is claimed is:

1. A process for producing cycloalkanol and/or cycloalkanone, which comprises oxidizing cycloalkane with oxygen in the presence of mesoporous silica, wherein
(1) the mesoporous silica contains at least one transition metal, and
(2) a ratio of total volume of mesoporous silica particles having a particle diameter of 20 μm or less to total volume of entire mesoporous silica particles is 25% or more in the mesoporous silica, and
wherein the mesoporous silica is mesoporous silica obtained by mixing tetraalkoxysilane, a structure-directing agent, ammonia, alcohol and water and calcining the obtained solid.

2. The process according to claim 1, wherein the transition metal is at least one metal selected from the group consisting of vanadium, chromium, manganese, iron, cobalt, ruthenium and palladium.

3. The process according to claim 1, wherein the transition metal is cobalt.

4. The process according to any one of claims 1 to 3, wherein the mesoporous silica is a MCM-41 type mesoporous silica.

5. The process according to any one of claims 1 to 3, wherein the mesoporous silica is the one which is subjected to a contact treatment with an organosilicon compound represented by the following formula (I):

Si(R$^1$)$_x$(R$^2$)$_{4-x}$ (I)

wherein R$^1$ represents an alkoxy group, hydroxy group or a halogen atom, R$^2$ represents an alkoxy group, an alkyl group, an allyl group, an aryl group or an aralkyl group, and x represents a number of 1 to 3.

6. The process according claim 5, wherein the organosilicon compound is trialkoxyalkylsilane or tetraalkoxysilane.

7. The process according to any one of claims 1 to 3, wherein the cycloalkane is cyclohexane.

* * * * *